US010420908B2

(12) United States Patent
Chodkowski et al.

(10) Patent No.: US 10,420,908 B2
(45) Date of Patent: Sep. 24, 2019

(54) MOTION LIMITING COUPLING ASSEMBLY FOR A PATIENT INTERFACE

(71) Applicant: KONINKLIJKE PHILIPS N.V., Eindhoven (NL)

(72) Inventors: Lauren Patricia Chodkowski, Pittsburgh, PA (US); Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1192 days.

(21) Appl. No.: 14/398,890

(22) PCT Filed: Apr. 25, 2013

(86) PCT No.: PCT/IB2013/053270
§ 371 (c)(1),
(2) Date: Nov. 4, 2014

(87) PCT Pub. No.: WO2013/168041
PCT Pub. Date: Nov. 14, 2013

(65) Prior Publication Data
US 2015/0114398 A1 Apr. 30, 2015

Related U.S. Application Data

(60) Provisional application No. 61/643,983, filed on May 8, 2012.

(51) Int. Cl.
*A61M 16/08* (2006.01)
*A61M 16/06* (2006.01)

(52) U.S. Cl.
CPC .... *A61M 16/0816* (2013.01); *A61M 16/0605* (2014.02); *A61M 16/0622* (2014.02); *A61M 16/0683* (2013.01); *A61M 2205/02* (2013.01)

(58) Field of Classification Search
CPC .......... A61M 16/0816; A61M 16/0605; A61M 16/0622; A61M 16/0683; A61M 2205/02
See application file for complete search history.

(56) References Cited

U.S. PATENT DOCUMENTS 4,305,160 A * 12/1981 Sundahl ................. A42B 3/222
    16/334
4,807,305 A * 2/1989 Sundahl ................. A42B 3/223
    2/424

(Continued)

*Primary Examiner* — Tan-Uyen T Ho
*Assistant Examiner* — Jonathan S Paciorek
(74) *Attorney, Agent, or Firm* — Michael W. Haas

(57) ABSTRACT

A coupling assembly for a respiratory interface device support assembly and a respiratory interface device mask is provided. The respiratory interface device support assembly has at least one strap structured to be coupled to each lateral side of the respiratory interface device mask. The coupling assembly includes a first rotatable coupling component structured to be coupled to the support assembly and having a first rotation limiting structure, and, a second rotatable coupling component structured to be coupled to the mask and having a second rotation limiting structure. When coupled, the first rotatable coupling component first rotation limiting structure and the second rotatable coupling component first rotation limiting structure limit the rotation of the first rotatable coupling component relative to the second rotatable coupling component.

15 Claims, 4 Drawing Sheets

(56) References Cited

U.S. PATENT DOCUMENTS

| | | | |
|---|---|---|---|
| 5,091,997 A * | 3/1992 | Foehl | A42B 3/222 |
| | | | 2/424 |
| 2003/0154984 A1* | 8/2003 | Fernandes | A41D 13/1146 |
| | | | D24/110.1 |
| 2003/0196658 A1* | 10/2003 | Ging | A61M 16/06 |
| | | | 128/201.22 |
| 2005/0155604 A1* | 7/2005 | Ging | A44B 11/266 |
| | | | 128/206.21 |
| 2005/0199242 A1* | 9/2005 | Matula, Jr. | A61M 16/06 |
| | | | 128/207.13 |
| 2006/0162729 A1 | 7/2006 | Ging | |
| 2006/0283461 A1* | 12/2006 | Lubke | A61M 16/06 |
| | | | 128/207.11 |
| 2007/0044797 A1 | 3/2007 | Ho | |
| 2007/0144525 A1 | 6/2007 | Davidson | |
| 2009/0032026 A1 | 2/2009 | Price | |
| 2009/0044808 A1* | 2/2009 | Guney | A61M 16/0666 |
| | | | 128/206.24 |
| 2009/0044809 A1* | 2/2009 | Welchel | A41D 13/1161 |
| | | | 128/206.27 |
| 2011/0023883 A1 | 2/2011 | Hieber | |
| 2012/0041331 A1 | 2/2012 | Burton | |

* cited by examiner

MOTION LIMITING COUPLING ASSEMBLY FOR A PATIENT INTERFACE

CROSS-REFERENCE TO RELATED APPLICATIONS

This patent application claims priority benefit under 35 U.S.C. § 371 of international patent applications no. PCT/IB2013/053270, filed Apr. 25, 2013, which claims the priority benefit under 35 U.S.C. § 119(e) of U.S. Provisional Application No. 61/643,983 filed on May 3, 2012, the contents of which are herein incorporated by reference.

BACKGROUND OF THE INVENTION

1. Field of the Invention

The present invention relates to respiratory interface devices for transporting a gas to and/or from an airway of a user which include, but are not limited to, a mask and a support assembly with a coupling assembly structured to couple the mask and support assembly and wherein the coupling assembly is further structured to limit the rotation of the mask relative to the support assembly.

2. Description of the Related Art

Masks for respiratory interface devices may include a relatively rigid faceplate and a softer patient contacting cushion. The mask is positioned over a user's nose and/or mouth and held in place by a support assembly. A support assembly includes at least one strap structured to extend about the user's head. The straps are coupled to the mask at a coupling. For example, the coupling between the mask and support assembly may be an elongated slot on the mask. The end of a flexible strap extends through, and is looped about, the slot. This type of coupling allows for limited rotation of the strap relative to the mask. The rotation is about an axis parallel to the slot. Another coupling assembly may be snaps mounted on the straps and mask. Such couplings allow for rotation about an axis extending perpendicular to the plane of the snap elements. Another type of coupling assembly is similar to a button. That is, a post with a cap extends from the mask and the strap includes a corresponding opening disposed at a vertex. That is, the strap is, for example, "V" shaped. The strap opening extends to the edge of the strap. A user then positions the post in the pocket defined by the V-shaped strap and allows the post to enter the opening. This coupling allows the mask to rotate about an axis parallel to the axis of the post.

With a slot coupling, the rotation of the mask relative to the straps is very limited. That is, the limited rotation about an axis parallel to the slot generally does not permit the mask to rotate relative to the support assembly. With snaps, each strap end in the support assembly may have a coupling. For example, if the support assembly has two straps that are coupled to each side of the mask, i.e. there are four coupling locations, one at each end of each strap, and each coupling location has a snap. In this configuration, the support assembly may become tangled when disengaged from the mask or otherwise be confusing to the user when attempting to couple each coupling at the proper location. Further, snaps are subject to free rotation. The post and V-shaped strap coupling may reduce the number of coupling points, but is also subject to free rotation.

Each of these types of couplings has disadvantages. That is, it is desirable to have a mask rotate within a limited range relative to the support assembly so that the mask consistently provides a tangent seat relative to the user's face. A strap and slot coupling does not allow for sufficient rotation. That is, if the configuration of the support assembly does not position the mask so as to provide a seat that is tangent relative to the user's face, the mask may not be rotated relative to the support assembly and the mask may not provide a complete seal against the user's face. Snaps and post couplings, on the other hand, allow free rotation meaning the mask may move beyond a configuration where the mask provides a seat that is tangent relative to the user's face. For example, a child may not like the straps rubbing their ears and reposition the straps closer to the top of their head. In this configuration, the mask is being pulled upwardly and may not provide a seat that is tangent relative to the user's face. In this configuration, the mask may not provide a complete seal against the user's face. Further, such free rotation allows the mask to rotate freely while not in use and may allow the support assembly to become tangled.

SUMMARY OF THE INVENTION

A coupling assembly for a respiratory interface device support assembly and a respiratory interface device mask is provided. The respiratory interface device support assembly has at least one strap structured to be coupled to each lateral side of the respiratory interface device mask. The coupling assembly includes a first rotatable coupling component structured to be coupled to the support assembly and having a first rotation limiting structure, and, a second rotatable coupling component structured to be coupled to the mask and having a second rotation limiting structure. When coupled, the first rotation limiting structure and the second rotation limiting structure limit the rotation of the first rotatable coupling component relative to the second rotatable coupling component.

It is a further object of this invention to provide a method of using a respiratory interface device support cushion described above, the method including the steps of limiting the rotation of coupling assembly first rotatable coupling component relative to the second rotatable coupling component, positioning the mask over the user's face, coupling a strap to each coupling assembly, and orienting the mask so as to be substantially tangent to the user's face.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
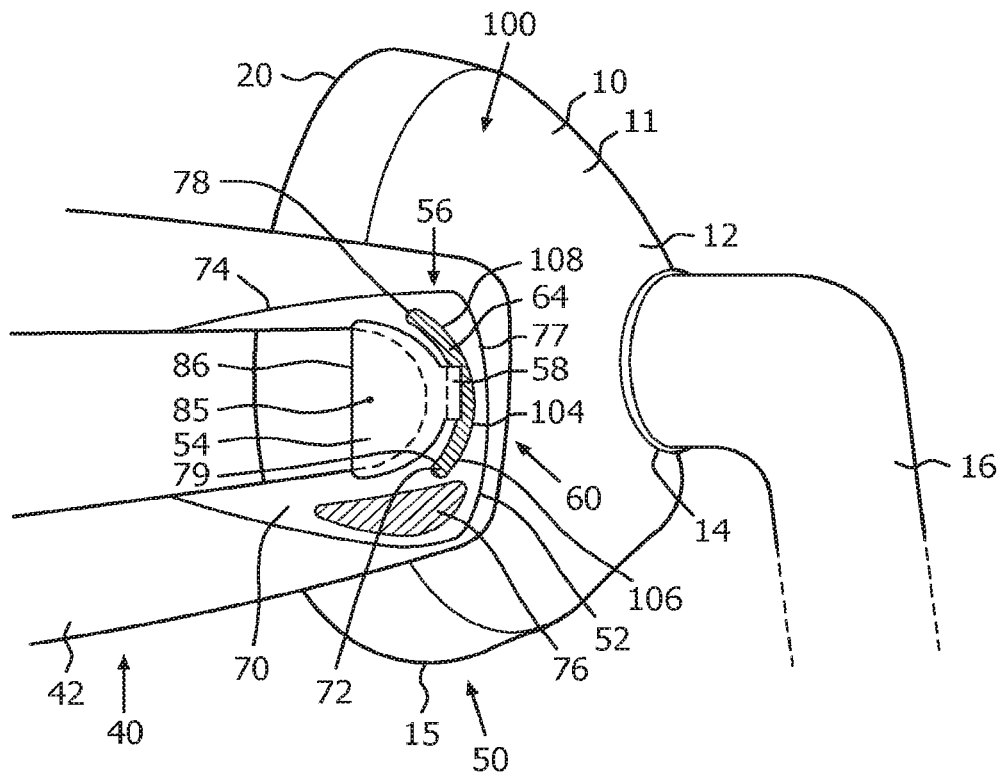
FIG. 1 is an isometric view of an embodiment of a respiratory interface device.

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, "a generally continuous seal" may have a gap or may gap when the user moves. As used herein, "a more complete seal" has a gap that is shorter in length than a gap of a generally continuous seal, or, is resistant to gapping when the user moves.

As used herein, "correspond" indicates that two structural components are sized to engage each other with a minimum amount of friction. Thus, an opening which corresponds to a member is sized slightly larger than the member so that the member may pass through the opening with a minimum amount of friction. This definition is modified if the two components are said to fit "snugly" together. In that situation, the difference between the size of the components is even smaller whereby the amount of friction increases.

As used herein, a "coupling component" is one element of a coupling assembly. That is, a coupling assembly includes at least two elements, or components, that are structured to be coupled together. It is understood that the elements of a coupling assembly correspond to each other or are otherwise structured to be joined together. For example, in a coupling assembly, if one coupling element is a bolt, the other coupling element is a nut. Further, it is understood that the two elements of a coupling assembly may not be described at the same time.

As used herein, "generally tangent relative to the user's face" means that the sealing element is seated.

FIG. 1 shows a respiratory interface device 8 according to an exemplary embodiment of the invention. Respiratory interface device 8 includes a respiratory mask 10 and a support assembly 40. Mask 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g., an auto-titrating device, proportional assist ventilation (PAV™) device, proportional positive airway pressure (PPAP) device, C-Flex™ device, Bi-Flex™ device, or a BiPAP™ device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory mask 10 includes a body 11 with a faceplate 12 and a cushion 15, discussed below. In an exemplary embodiment, faceplate 12 is substantially rigid. In an exemplary embodiment, shown in FIG. 1, faceplate 12 is a single piece structured to cover the user's nose and mouth. That is, mask 10 has a peripheral contour that is structured to extend over a user's nose and mouth. In this embodiment, body 11 is coextensive with faceplate 12. It is understood that this is an exemplary embodiment and a mask may be structured to extend over just the user's nose, or, just the user's mouth. Faceplate 12 defines lower opening 14. Lower opening 14 can function as a gas inlet. Gas inlet (lower opening 14) can be coupled to a coupling device 16, such as a swivel conduit, for carrying gas such as air between mask 10 and an external gas source (not shown), such as a blower, or any other suitable device.

It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 16, shown in FIG. 1, is not meant to be limiting and it should be understood that the present invention contemplates a variety of different coupling devices that could be attached, either permanently or selectively, to lower opening 14 to carry gas to or from mask 10. Thus, a variety of coupling devices (e.g., with or without swivels on one or both ends, and with or without an exhalation system formed integral to the device) may be substituted for coupling device 16.

Cushion 15 is structured to extend from faceplate 12 toward the user's face and generally defines the depth of mask 10. Cushion 15 includes a cushion body 20 made from a flexible material. Cushion 15 is structured to engage the user's face and provide a generally continuous seal. This seal may be improved to be a more complete seal if mask 10 is maintained in an orientation that is generally tangent relative to the user's face. The bias that causes cushion 15 to engage the user's face is created by support assembly 40.

Support assembly 40 includes at least one strap 42 structured to extend about the user's head. As is known, support assembly straps 42 may form a web (not shown) having straps 42 in any number of configuration. In an exemplary embodiment, and as shown in the FIGS. 1 and 3, two straps 42 are used; the claims, however, are not limited to this configuration. Straps 42 may be made from an elastic or non-elastic material.

A coupling assembly 50 is disposed on each lateral side of mask 10. Each coupling assembly 50 is substantially similar and therefore only one of each coupling assembly 50 will be discussed below. It is understood, however, that the description is applicable to each coupling assembly 50.

Coupling assembly 50 is structured to couple support assembly 40 to mask 10. In an exemplary embodiment, there are two coupling assemblies, one disposed on each lateral side of mask 10, i.e., generally on the right and left sides of mask 10. Each coupling assembly 50 includes a first rotatable coupling component 52 and a second rotatable coupling component 54. First rotatable coupling component 52 is structured to be coupled to support assembly 40. Second rotatable coupling component 54 is structured to be coupled to mask 10. First rotatable coupling component 52 and second rotatable coupling component 54 have cooperative rotation limiting structures 56, 58. That is, first rotatable coupling component 52 includes a first rotation limiting structure 56 and second rotatable coupling component 54 includes a second rotation limiting structure 58. When first rotatable coupling component 52 and second rotatable coupling component 54 are coupled, first rotatable coupling component first rotation limiting structure 56 and second rotatable coupling component first rotation limiting structure 58 limit the rotation of first rotatable coupling component 52 relative to the second rotatable coupling component 54. In an exemplary embodiment, the rotation of first rotatable coupling component 52 relative to second rotatable coupling component 54 is limited to an arc of between about 0 and 45 degrees.

Further, first rotatable coupling component 52 and second rotatable coupling component 54 may include a cooperative positioning device 60. Cooperative positioning device 60 is structured to maintain the position of first rotatable coupling component 52 relative to the second rotatable coupling component 54. As discussed below, and in one exemplary embodiment, cooperative positioning device 60 may include at least one flexible tooth 62 and a rack 64. In another exemplary embodiment, cooperative positioning device 60 may include a friction increasing material.

An exemplary embodiment of coupling assembly 50 is shown in FIG. 1. In this embodiment, first rotatable coupling component 52 includes a planar body 70 having an arcuate groove 72 therein. First rotatable coupling component body 70 is coupled to support assembly 40. As shown, first rotatable coupling component body 70 is adhered to straps 42. First rotatable coupling component body 70 may be structured to position straps 42. In one exemplary embodiment, first rotatable coupling component body 70 has first end 74 and a second end 76. First rotatable coupling component body first end 74 and second end 76 are structured to be coupled to support assembly at least one strap 42.

In one exemplary embodiment, first rotatable coupling component body 70 is generally U-shaped. That is, first rotatable coupling component body first end 74 and second end 76, i.e., the tips of the U-shape, extend toward the user's ear when mask 10 is in use. A middle portion 78 of rotatable coupling component body 70 extends vertically, thereby spacing straps 42. Further, the angle of first rotatable coupling component body first end 74 and second end 76 relative to first rotatable coupling component body middle portion 77 may position straps 42 at a selected location on the user's head. Further, the position of straps 42 is effected by the vertical length of first rotatable coupling component body 70. In this embodiment, first rotatable coupling component body 70 has a vertical length of between 0.5 and 3.0 inches. Thus, the angle and spacing of first rotatable coupling component body first end 74 and second end 76 position straps 42 on the user's head.

Rotatable coupling component body groove 72 is disposed on one planar face of first rotatable coupling component body 70 (the outer face as shown in FIG. 1). Rotatable coupling component body groove 72 extends over an arc of between about 0 and 45 degrees. Rotatable coupling component body groove 72 has a "floor" 73 which, as used herein, is the surface at the deepest elevation of rotatable coupling component body groove 72. If rotatable coupling component body groove 72 does not have a flat bottom, e.g., rotatable coupling component body groove 72 has a V-shaped cross-section, then floor 73 includes a portion of rotatable coupling component body groove 72 sidewalls. Rotatable coupling component body groove 72 has a first end 78 and a second end 79. That is, rotatable coupling component body groove 72 does not have open ends.

Figure 2:
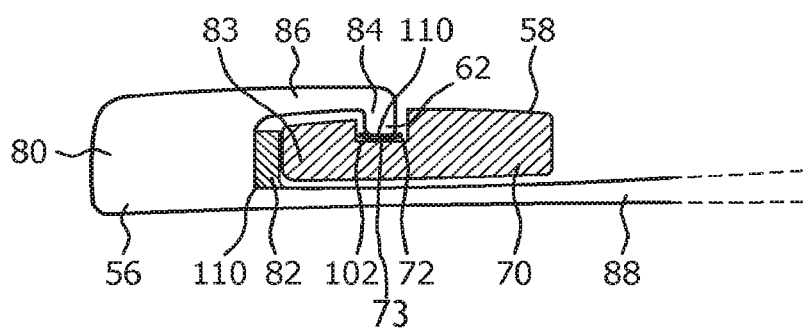
FIG. 2 is a detail cross-sectional view of a portion of the a respiratory interface device in FIG. 1.

Further, in the exemplary embodiment of coupling assembly 50 shown in FIG. 1, second rotatable coupling component 52 includes a body 80 having a pocket 82 (FIG. 2) and a flexible tab 84 (FIG. 2). Second rotatable coupling component pocket 82 is open on three contiguous sides and is sized to correspond to the thickness of first rotatable coupling component body 70. In this configuration, second rotatable coupling component pocket 82 is similar to a groove that is open on both ends. Second rotatable coupling component pocket 82 has a rotation surface 83 that is arcuate. Thus, second rotatable coupling component pocket rotation surface 83 has a center 85. As shown, tab 84 extends inwardly, i.e., toward the user's face, from a second rotatable coupling component body outer planar member 86. In another embodiment (nor shown), first rotatable coupling component body groove 72 is disposed on the inner face of first rotatable coupling component body 70 and tab 84 extends outwardly, i.e., away from the user's face, from a second rotatable coupling component body inner planar member 88. Regardless of the location of tab 84 relative to second rotatable coupling component body 80, tab 84 is positioned to extend into first rotatable coupling component body groove 72 when first rotatable coupling component 52 and second rotatable coupling component 54 are coupled.

In the exemplary embodiment of coupling assembly 50 shown in FIG. 1, first rotation limiting structure 56 is first rotatable coupling component body groove 72, and, second rotation limiting structure 58 is second rotatable coupling component body tab 84. That is, when first rotatable coupling component 52 and second rotatable coupling component 54 are coupled, first rotatable coupling component body 70 is disposed in second rotatable coupling component body pocket 82 with second rotatable coupling component body tab 84 disposed in first rotatable coupling component body groove 72. In this configuration, first rotatable coupling component body 70 is disposed adjacent to, and may engage, second rotatable coupling component pocket rotation surface 83. Further, second rotatable coupling component body tab 84 extends into groove 72. In this configuration, first rotatable coupling component body 70 is structured to pivot about second rotatable coupling component pocket rotation surface center 85.

The relative rotation of first rotatable coupling component 52 and second rotatable coupling component 54 is limited due to second rotatable coupling component body tab 84 engaging one of rotatable coupling component body groove first end 78 or second end 79. That is, first rotatable coupling component 52 and second rotatable coupling component 54 may rotate generally freely relative to each other so long as second rotatable coupling component body tab 84 is not at either rotatable coupling component body groove first end 78 or second end 79. When second rotatable coupling component body tab 84 is at either rotatable coupling component body groove first end 78 or second end 79, second rotatable coupling component body tab 84 engages the rotatable coupling component body groove first end 78 or second end 79 thereby preventing further rotation. Thus, the interaction of second rotatable coupling component body tab 84 and the ends 78, 79 of first rotatable coupling component body groove 72 limit the rotation of first rotatable coupling component 52 relative to second rotatable coupling component 54.

Further, coupling assembly 50 may include a cooperative positioning device 100. Cooperative positioning device 100 is structured to maintain the orientation of first rotatable coupling component 52 relative to second rotatable coupling component 54, unless a bias is applied by a user. For example, in the exemplary embodiment of coupling assembly 50 shown in FIG. 2, second rotatable coupling component body pocket 82 may be sized to provide a snug fit when first rotatable coupling component body 70 is disposed therein. With a snug fit, friction between first rotatable coupling component 52 and second rotatable coupling component 54 will maintain the orientation of first rotatable coupling component 52 relative to second rotatable coupling component 54, unless a bias is applied by a user.

Further, in the exemplary embodiment of coupling assembly 50 shown in FIG. 1, cooperative positioning device 100 may include at least one flexible tooth 102 and a rack 104. Rack 104 includes a plurality of teeth 106 defining grooves 108 therebetween. At least one flexible tooth 102 is sized to correspond to rack 104. That is, at least one flexible tooth 102 is sized to fit within rack grooves 108. At least one flexible tooth 102 is disposed at the distal end of second rotatable coupling component body tab 84 and extends toward rack 104. As shown, rack 104 is disposed on first rotatable coupling component body groove floor 73. It is noted, however, that rack 104 may be disposed on the sides of first rotatable coupling component body groove 72. When second rotatable coupling component body tab 84 is disposed in first rotatable coupling component body groove 72, at least one flexible tooth 102 engages rack 104 and will maintain the orientation of first rotatable coupling component 52 relative to second rotatable coupling component 54, unless a bias is applied by a user. When a user applies bias to second rotatable coupling component 54, e.g., by tilting mask 10, then at least one flexible tooth 102 flexes and moves over rack teeth 106 until the bias is relieved.

In an alternative exemplary embodiment, shown in FIG. 2, cooperative positioning device 100 may include a friction increasing material 110 disposed in first rotatable coupling component body groove 72 and, in an exemplary embodiment, on first rotatable coupling component body groove floor 73. In this embodiment, second rotatable coupling component body tab 84 is structured to engage friction increasing material 110. That is, second rotatable coupling component body tab 84 extends into first rotatable coupling component body groove 72 a sufficient distance so as to contact friction increasing material 110. In another alternative, friction increasing material 110 may be disposed between first rotatable coupling component 52 and second rotatable coupling component 54, e.g., on second rotatable coupling component pocket rotation surface 83. The increased friction between first rotatable coupling component 52 and second rotatable coupling component 54 will maintain the orientation of first rotatable coupling component 52 relative to second rotatable coupling component 54, unless a bias is applied by a user. Friction increasing material 110 may be, but is not limited to, silicon.

Figure 3:
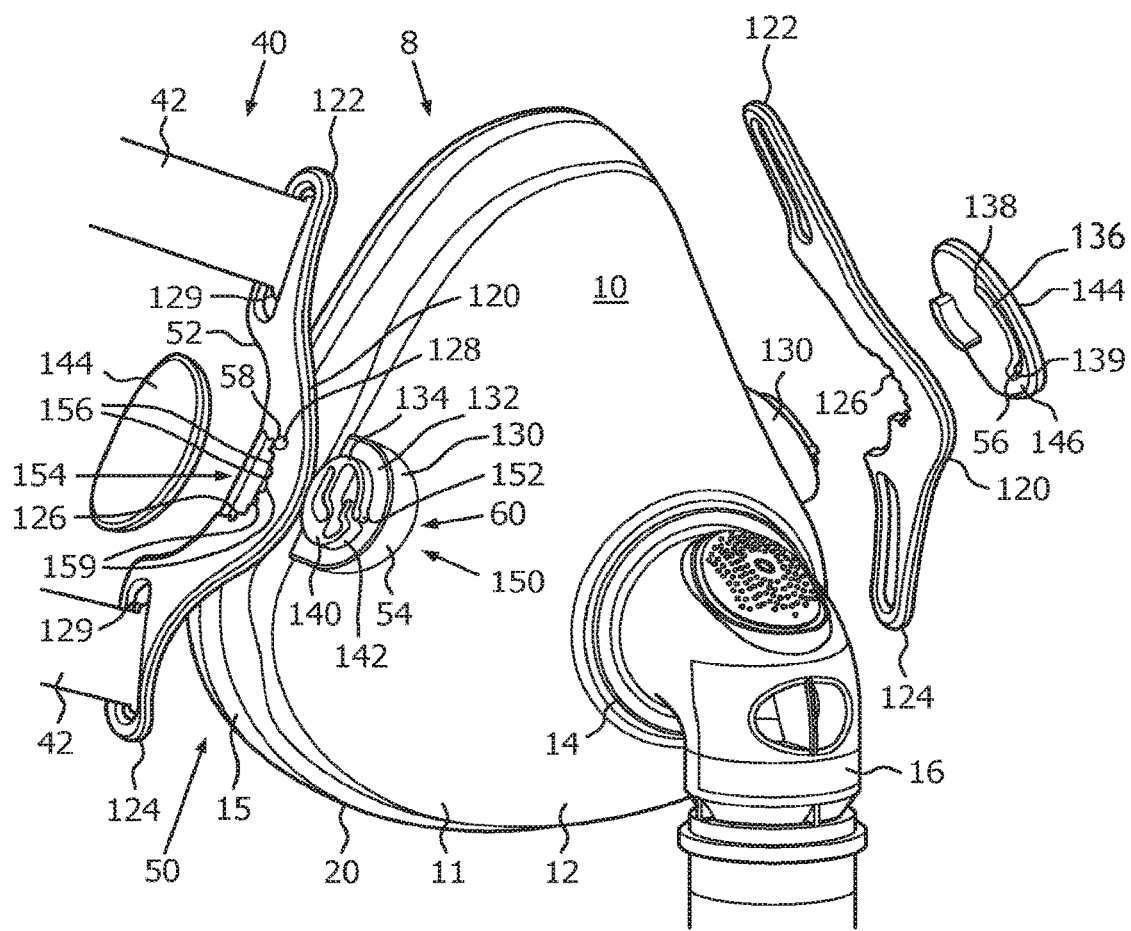
FIG. 3 is an isometric view of another embodiment of a respiratory interface device.

In another exemplary embodiment of coupling assembly 50, shown in FIG. 3, first rotatable coupling component 52 includes an elongated planar body 120 having a first end 122 and a second end 124, an arcuate contact surface 126 disposed between the first and second ends 122, 124, and a projection 128 extending from one of the first rotatable coupling component body planar surfaces. First rotatable coupling component body arcuate contact surface 126 is not disposed on one of the first rotatable coupling component body 120 planar surfaces, but rather one of the lateral sides of first rotatable coupling component body 120. First rotatable coupling component body arcuate contact surface 126 is shaped to correspond to second rotatable coupling component body arcuate protrusion sidewall 142, discussed below. First rotatable coupling component body first end 122 and second end 124 are each structured to be coupled to strap 42. As shown, the strap coupling is a slot 129 through which strap 42 may be looped, however, any type of strap 42 coupling may be used. In this exemplary embodiment, first rotatable coupling component body 120 has a vertical length of between 1.5 and 4.0 inches. First rotatable coupling component body projection 128 is sized to correspond to second rotatable coupling component body groove 136, discussed below.

Second rotatable coupling component 54 includes a body 130 defining a planar rotation surface 132, an arcuate protrusion 134 therefrom, and an arcuate groove 136. Second rotatable coupling component body arcuate protrusion 134 is a planar protrusion. As used herein, a "planar protrusion" is a planar member having a surface that is generally parallel to the surface from which it protrudes and side walls that are generally perpendicular to the surface from which it protrudes. Thus, second rotatable coupling component body arcuate protrusion 134 has a planar surface 140 generally parallel to the second rotatable coupling component body planar rotation surface 132 and a sidewall 142 that is generally perpendicular to second rotatable coupling component body planar rotation surface 132. Second rotatable coupling component body arcuate protrusion sidewall 142 is substantially arcuate and has a center. Second rotatable coupling component body arcuate groove 136 has a first end 138 and a second end 139.

Second rotatable coupling component body 130 may include a flange (not shown) at the upper, outer edge of second rotatable coupling component body arcuate protrusion sidewall 142. Such a flange would extend generally parallel to second rotatable coupling component body planar rotation surface 132 and be structured to trap first rotatable coupling component body 120 between flange and second rotatable coupling component body planar rotation surface 132. As shown, second rotatable coupling component 54 may include a cap 144 disposed over second rotatable coupling component body arcuate protrusion 134. Cap 144 has a planer inner surface 146. Cap planar inner surface 146 extends substantially parallel to second rotatable coupling component body rotation surface 132. The gap between cap planer inner surface 146 and second rotatable coupling component body rotation surface 132 is sized to correspond to the thickness of first rotatable coupling component body 120. That is, second rotatable coupling component body arcuate protrusion 134 has a height above second rotatable coupling component body rotation surface 132 that corresponds to the thickness of first rotatable coupling component body 120.

Second rotatable coupling component body groove 136 may be disposed on either cap planer inner surface 146 (as shown) or second rotatable coupling component body rotation surface 132 (not shown). First rotatable coupling component body projection 128 is positioned on the planar surface of first rotatable coupling component body 120 that abuts the surface of second rotatable coupling component body 130 having second rotatable coupling component body groove 136.

In this configuration, first rotation limiting structure is first rotatable coupling component body projection 128 and second rotation limiting structure is second rotatable coupling component body groove 136. That is, first rotatable coupling component body 120 is disposed on second rotatable coupling component body rotation surface 132 with first rotatable coupling component projection 128 disposed in second rotatable coupling component body groove 136. The relative rotation of first rotatable coupling component 52 and second rotatable coupling component 54 is limited due to first rotatable coupling component body projection 128 engaging one of second rotatable coupling component body groove first end 138 or second end 139. That is, first rotatable coupling component 52 and second rotatable coupling component 54 may rotate generally freely relative to each other so long as first rotatable coupling component body projection 128 is not at either second rotatable coupling component body groove first end 138 or second end 139.

When first rotatable coupling component body projection 128 is at either second rotatable coupling component body groove first end 138 or second end 139, first rotatable coupling component body projection 128 engages the second rotatable coupling component body groove first end 138 or second end 139 thereby preventing further rotation. Thus, the interaction of first rotatable coupling component body projection 128 and the ends 138, 139 of second rotatable coupling component body groove 136 limit the rotation of first rotatable coupling component 52 relative to second rotatable coupling component 54.

Figure 4:
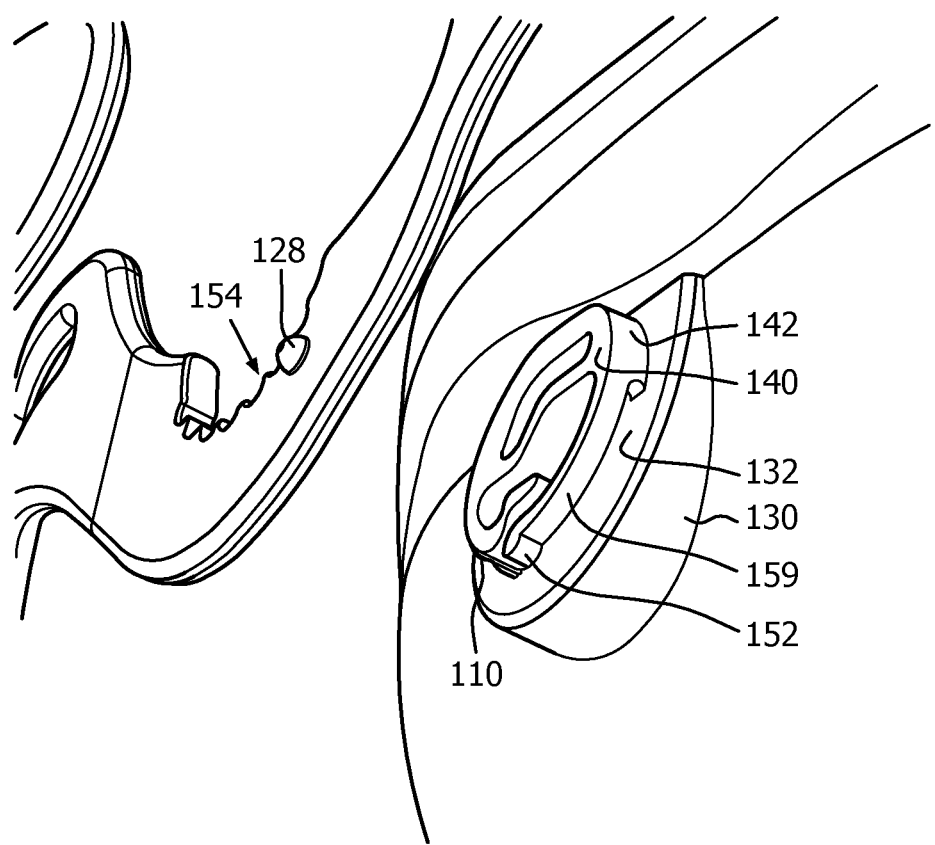
FIG. 4 is an detail isometric view of a portion of the a respiratory interface device in FIG. 3.

The exemplary embodiment of coupling assembly 50 shown in FIG. 3 may also include a cooperative positioning device 150. Having the gap between cap planer inner surface 146 and second rotatable coupling component body rotation surface 132 sized to snuggly correspond to the thickness of first rotatable coupling component body 120 may provide friction sufficient to maintain the orientation of first rotatable coupling component 52 relative to second rotatable coupling component 54, unless a bias is applied by a user. Alternatively, and in the exemplary embodiment of coupling assembly 50 shown in FIG. 3, cooperative positioning device 150 may include at least one flexible tooth 152 and a rack 154. Rack 154 includes a plurality of teeth 156 defining grooves 158 therebetween. At least one flexible tooth 152 is sized to correspond to rack 154. That is, at least one flexible tooth 152 is sized to fit within rack grooves 158. In this embodiment, second rotatable coupling component body arcuate protrusion sidewall 142 includes a portion that is a lever arm 159 (FIG. 4) or a cantilevered arm. Second rotatable coupling component body arcuate protrusion sidewall lever arm 159 is structured to move substantially radially relative to the center of second rotatable coupling component body arcuate protrusion sidewall 142. At least one flexible tooth 152 is disposed at the distal end of second rotatable coupling component body arcuate protrusion sidewall lever arm 159. At least one flexible tooth 152 projects radially outwardly from second rotatable coupling component body arcuate protrusion sidewall 142. That is, at least one flexible tooth 152 extends beyond the perimeter of second rotatable coupling component body arcuate protrusion sidewall 142.

Rack 154 is disposed on a portion of first rotatable coupling component body arcuate contact surface 126. When first rotatable coupling component 52 is disposed on second rotatable coupling component body rotation surface 132, i.e., in the gap between cap planer inner surface 146 and second rotatable coupling component body rotation surface 132, rack 154 is position adjacent second rotatable coupling component body arcuate protrusion sidewall lever arm 159. Thus, at least one flexible tooth 152 extends into rack 154 and is disposed in one of rack groove 158. In this configuration, the bias of second rotatable coupling component body arcuate protrusion sidewall lever arm 159 causing at least one flexible tooth 152 to engage rack 154 will maintain the orientation of first rotatable coupling component 52 relative to second rotatable coupling component 54, unless a bias is applied by a user. When a user applies bias to first rotatable coupling component 52, e.g., by rotating first rotatable coupling component body 120 about the center of second rotatable coupling component body arcuate protrusion sidewall 142, then second rotatable coupling component body arcuate protrusion sidewall lever arm 159 flexes and at least one flexible tooth 152 moves over rack teeth 106 until the bias is relieved.

In alternative embodiment, cooperative positioning device 150 includes a friction increasing material 110 (FIG. 4) disposed on second rotatable coupling component body arcuate protrusion sidewall 142. In this configuration, first rotatable coupling component body 120, and more specifically first rotatable coupling component body arcuate contact surface 126, engages friction increasing material 110. The increased friction between first rotatable coupling component 52 and second rotatable coupling component 54 will maintain the orientation of first rotatable coupling component 52 relative to second rotatable coupling component 54, unless a bias is applied by a user.

Figure 5:
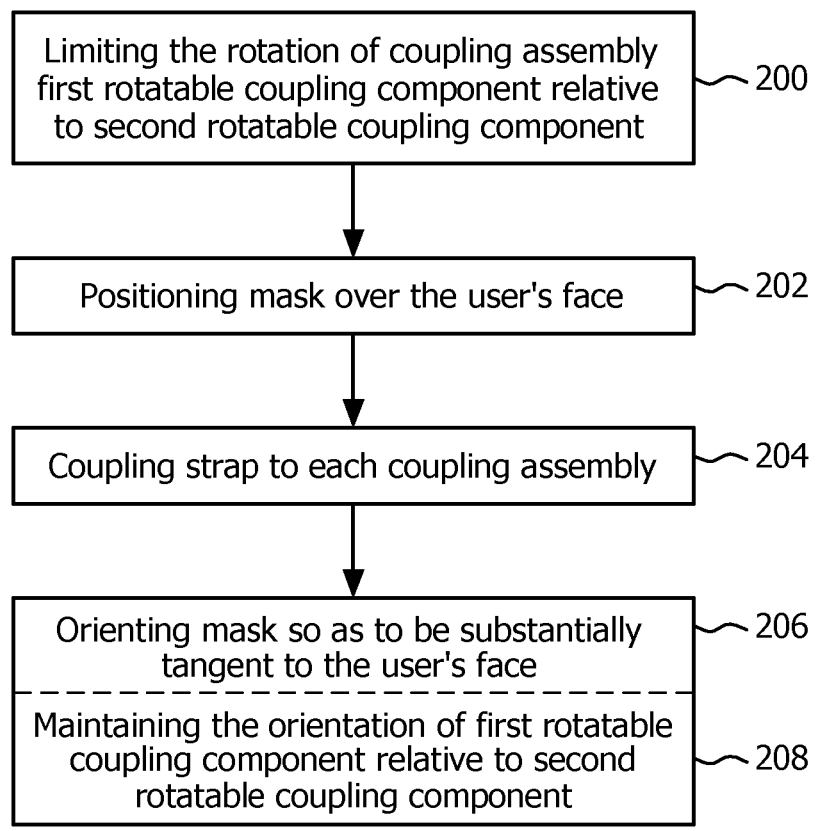
FIG. 5 is a flow chart of the steps for the method associated with the respiratory interface device.

Accordingly, and as shown in FIG. 5, a method of using coupling assembly 50 described above includes the steps of limiting 200 the rotation of coupling assembly first rotatable coupling component 52 relative to second rotatable coupling component 54, positioning 202 mask 10 over the user's face, coupling 204 strap 42 to each coupling assembly 50, and orienting 206 mask 10 so as to be substantially tangent to the user's face. The step of orienting 206 mask 10 so as to be substantially tangent to the user's face includes the further step of maintaining 208 the orientation of first rotatable coupling component 52 relative to second rotatable coupling component 54. That is, as described above, if a user attempts to over-rotate first rotatable coupling component 52 relative to second rotatable coupling component 54, an element, e.g., second rotatable coupling component body tab 84 or first rotatable coupling component body projection 128, engages one end 74, 76, 138, 139 of a groove, e.g., first rotatable coupling component body groove 72 or second rotatable coupling component body groove 136, thereby limiting the motion of first rotatable coupling component 52 relative to second rotatable coupling component 54.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A coupling assembly for a respiratory interface device support assembly and a respiratory interface device mask, the respiratory interface device support assembly having at least one strap structured to be coupled to each lateral side of the respiratory interface device mask, the coupling assembly comprising:
   a first rotatable coupling component structured to be coupled to the support assembly and having a first rotation limiting structure;
   a second rotatable coupling component structured to be coupled to the mask and having a second rotation limiting structure, wherein, when coupled, the first rotation limiting structure and the second rotation limiting structure limit the rotation of the first rotatable coupling component relative to the second rotatable coupling component; and
   wherein the rotation of the first rotatable coupling component relative to the second rotatable coupling component is limited to an arc of between about 0 and 45 degrees.

2. The coupling assembly of claim 1, wherein the first rotatable coupling component and the second rotatable coupling component include a cooperative positioning device.

3. The coupling assembly of claim 2, wherein the cooperative positioning device includes at least one flexible tooth and a rack.

4. The coupling assembly of claim 2, wherein the cooperative positioning device includes a friction increasing material.

5. The coupling assembly of claim 1, wherein: the first rotatable coupling component includes a planar body having an arcuate groove therein, the planar body coupled to the support assembly; and the second rotatable coupling component includes a body having a pocket and a flexible tab, the pocket sized to correspond to the thickness of the first rotatable coupling component body and the tab positioned to extend into the first rotatable coupling component body groove; the first rotation limiting structure being the first rotatable coupling component body groove; the second rotation limiting structure being the second rotatable coupling component body tab; the first rotatable coupling component body being disposed in the second rotatable coupling component body pocket with the second rotatable coupling component body tab disposed in the first rotatable coupling component body groove, the interaction of the second rotatable coupling component body tab and the ends of first rotatable coupling component body groove limiting the rotation of the first rotatable coupling component body relative to the second rotatable coupling component body.

6. The coupling assembly of claim 5, wherein: the first rotatable coupling component body has first end and a second end, and, a vertical length of between 0.5 and 3.0 inches; and the first rotatable coupling component body first end and second end being structured to be coupled to the support assembly at least one strap.

7. The coupling assembly of claim 5, wherein the first rotatable coupling component and the second rotatable coupling component include a cooperative positioning device.

8. The coupling assembly of claim 7, wherein: the cooperative positioning device includes a friction increasing material; the friction increasing material being disposed on the floor of the first rotatable coupling component body groove; the second rotatable coupling component body tab extending into the first rotatable coupling component body groove a sufficient distance so as to contact the friction increasing material.

9. The coupling assembly of claim 1, wherein: the first rotatable coupling component includes an elongated planar body having a first end and a second end, an arcuate contact surface disposed between the first and second ends, and a projection extending from one of the first rotatable coupling component body planar surfaces; the second rotatable coupling component includes a body defining a planar rotation surface, an arcuate protrusion therefrom, and an arcuate groove; the first rotation limiting structure being the first rotatable coupling component projection; the second rotation limiting structure being the second rotatable coupling component body groove; the first rotatable coupling component body disposed on the second rotatable coupling component body rotation surface with the first rotatable coupling component projection disposed in the second rotatable coupling component body groove.

10. The coupling assembly of claim 9, wherein: the second rotatable coupling component includes a cap disposed over the second rotatable coupling component body arcuate protrusion, the cap having a planer inner surface, the cap planar inner surface extending substantially parallel to the second rotatable coupling component body rotation surface; the first rotatable coupling component body disposed in the gap between the cap planar inner surface and the second rotatable coupling component body rotation surface; the second rotatable coupling component body groove disposed on the cap planar inner surface.

11. The coupling assembly of claim 9, wherein: the first rotatable coupling component body has a vertical length of between 1.5 and 4.0 inches; and the first rotatable coupling component body first end and second end being structured to be coupled to the support assembly at least one strap.

12. The coupling assembly of claim 9, wherein the first rotatable coupling component and the second rotatable coupling component include a cooperative positioning device.

13. The coupling assembly of claim 12, the cooperative positioning device includes at least one flexible tooth and a rack; the first rotatable coupling component body arcuate contact surface defining the rack; the second rotatable coupling component body arcuate protrusion having at least one flexible tooth structured to engage the first rotatable coupling component body arcuate contact surface rack.

14. The coupling assembly of claim 12, the cooperative positioning device includes a friction increasing material; the friction increasing material being disposed on the second rotatable coupling component body arcuate protrusion sidewall; the first rotatable coupling component body arcuate contact surface structured to engage the friction increasing material.

15. A coupling assembly for a respiratory interface device support assembly and a respiratory interface device mask, the respiratory interface device support assembly having at least one strap structured to be coupled to each lateral side of the respiratory interface device mask, the coupling assembly comprising:
   a first rotatable coupling component structured to be coupled to the support assembly and having a first rotation limiting structure;

a second rotatable coupling component structured to be coupled to the mask and having a second rotation limiting structure, wherein, when coupled, the first rotation limiting structure and the second rotation limiting structure limit the rotation of the first rotatable coupling component relative to the second rotatable coupling component;

the first rotatable coupling component includes a planar body having an arcuate groove therein, the planar body coupled to the support assembly;

the second rotatable coupling component includes a body having a pocket and a flexible tab, the pocket sized to correspond to the thickness of the first rotatable coupling component body and the tab positioned to extend into the first rotatable coupling component body groove; the first rotation limiting structure being the first rotatable coupling component body groove; the second rotation limiting structure being the second rotatable coupling component body tab;

the first rotatable coupling component body being disposed in the second rotatable coupling component body pocket with the second rotatable coupling component body tab disposed in the first rotatable coupling component body groove, the interaction of the second rotatable coupling component body tab and the ends of first rotatable coupling component body groove limiting the rotation of the first rotatable coupling component body relative to the second rotatable coupling component body;

wherein the first rotatable coupling component and the second rotatable coupling component include a cooperative positioning device;

wherein the first rotatable coupling component groove has a floor; the cooperative positioning device includes at least one flexible tooth and a rack; the at least one tooth being disposed on the distal tip of the second rotatable coupling component body tab; and the rack being disposed upon the floor of the first rotatable coupling component body groove.

* * * * *